US00PP27721P3

(12) United States Plant Patent
Bernuetz

(10) Patent No.: US PP27,721 P3
(45) Date of Patent: Feb. 28, 2017

(54) *EUPHORBIA* PLANT NAMED 'BONPRI 9276'

(50) Latin Name: ***Euphorbia pulcherrima* Willd. ex *Klotzsch×Euphorbia cornastra***
Varietal Denomination: Bonpri 9276

(71) Applicant: Andrew Bernuetz, Silverdale (AU)

(72) Inventor: Andrew Bernuetz, Silverdale (AU)

(73) Assignee: Bonza Botanicals PTY. LTD., Yellow Rock, NSW (AU)

( * ) Notice: Subject to any disclaimer, the term of this patent is extended or adjusted under 35 U.S.C. 154(b) by 39 days.

(21) Appl. No.: 14/545,690

(22) Filed: Jun. 6, 2015

(65) Prior Publication Data

US 2016/0360672 P1 Dec. 8, 2016

(51) Int. Cl.
*A01H 5/02* (2006.01)

(52) U.S. Cl.
USPC ..... Plt./302

(58) Field of Classification Search
USPC ..... Plt./302
See application file for complete search history.

*Primary Examiner* — Keith Robinson
(74) *Attorney, Agent, or Firm* — C. A. Whealy

(57) ABSTRACT

A new and distinct cultivar of *Euphorbia* plant named 'Bonpri 9276', characterized by its upright and mounded plant habit; moderately vigorous growth habit; freely branching habit; dark green-colored leaves; inflorescences with dark pink-colored flower bracts; and good post-production longevity.

1 Drawing Sheet

Botanical designation: *Euphorbia pulcherrima* Willd. ex Klotzsch×*Euphorbia cornastra.*

Cultivar denomination: 'BONPRI 9276'.

CROSS-REFERENCED TO CLOSELY-RELATED APPLICATIONS

Title: *Euphorbia* Plant Named 'Bonpri 9172'
Applicant: Andrew Bernuetz
Filed: Concurrently with this application

BACKGROUND OF THE INVENTION

The present invention relates to a new and distinct cultivar of *Euphorbia* plant, an interspecific hybrid botanically known as *Euphorbia pulcherrima* Willd. ex Klotzsch×*Euphorbia cornastra*, and hereinafter referred to by the cultivar name 'Bonpri 9276'.

The new *Euphorbia* plant is a product of a planned breeding program conducted by the Inventor in Yellow Rock, New South Wales, Australia. The objective of the program is to create and develop new interspecific *Euphorbia* plants with compact, upright and mounded plant habit and attractive flower bracts.

The new *Euphorbia* plant is a naturally-occurring whole plant mutation of a proprietary selection of *Euphorbia pulcherrima* Willd. ex Klotzsch×*Euphorbia cornastra* identified as code number 574, not patented. The new *Euphorbia* plant was discovered and selected by the Inventor as a single flowering plant from within a population of plants of the proprietary selection in a controlled greenhouse environment in Yellow Rock, New South Wales, Australia in May, 2011.

Asexual reproduction of the new *Euphorbia* plant by terminal vegetative cuttings in a controlled greenhouse environment in Yellow Rock, New South Wales, Australia since June, 2011 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpri 9276'. These characteristics in combination distinguish 'Bonpri 9276' as a new and distinct *Euphorbia* plant:

1. Upright and mounded plant habit.
2. Moderately vigorous growth habit.
3. Freely branching habit.
4. Dark green-colored leaves.
5. Inflorescences with dark pink-colored flower bracts.
6. Good post-production longevity.

In side-by-side comparisons conducted in Yellow Rock, New South Wales, Australia, plants of the new *Euphorbia* differ primarily from plants of the parent selection in flower bract color as plants of the parent selection have hot pink-colored flower bracts.

Plants of the new *Euphorbia* can be compared to plants of *Euphorbia pulcherrima* Willd. ex Klotzsch×*Euphorbia cornastra* 'Bonpri 9172', disclosed in U.S. Plant patent application Ser. No. 14/545,689. In side-by-side comparisons conducted in Yellow Rock, New South Wales, Australia, plants of the new *Euphorbia* differ primarily from plants of 'Bonpri 9172' in flower bract color as plants of 'Bonpri 9172' have red-colored flower bracts.

Plants of the new *Euphorbia* can also be compared to plants of *Euphorbia pulcherrima* Willd. ex Klotzsch×*Euphorbia cornastra* 'Bonpridepcom', disclosed in U.S. Plant Pat. No. 21,324. In side-by-side comparisons conducted in Yellow Rock, New South Wales, Australia, plants of the new *Euphorbia* differed primarily from plants of 'Bonpridepcom' in the following characteristics:

1. Plants of the new *Euphorbia* had longer and thicker lateral branches than plants of 'Bonpridepcom'.
2. Plants of the new *Euphorbia* were more freely branching than plants of 'Bonpridepcom'.
3. Plants of the new *Euphorbia* had larger leaves than plants of 'Bonpridepcom'.
4. Plants of the new *Euphorbia* had more inflorescences than plants of 'Bonpridepcom'.
5. Plants of the new *Euphorbia* and 'Bonpridepcom' differ in flower bract color as plants of 'Bonpridepcom' have dark red purple-colored flower bracts.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the sheet comprises a side perspective view of a typical flowering plant of 'Bonpri 9276' grown in a container.

The photograph at the bottom of the sheet is a close-up view of a typical inflorescence of 'Bonpri 9276'.

DETAILED BOTANICAL DESCRIPTION

Plants used in the aforementioned photographs and herewith described in detail were grown during the autumn and winter in 12-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were four months old when the photographs and the description were taken. In the following description, color references are made to The Royal Horticultural Society Colour Chart, Fourth Edition, 2007, except where general terms of ordinary dictionary significance are used.

Botanical classification: *Euphorbia pulcherrima* Willd. ex Klotzsch×*Euphorbia cornastra* 'Bonpri 9276'.

Parentage: Naturally-occurring whole plant mutation of a proprietary selection of *Euphorbia pulcherrima* Willd. ex Klotzsch×*Euphorbia cornastra* identified as code number 574, not patented.

Propagation:

*Type*.—Terminal vegetative cuttings.

*Time to initiate roots, summer*.—About ten days at 18° C. to 25° C.

*Time to initiate roots, winter*.—About twelve days at 16° C. to 20° C.

*Time to produce a rooted young plant, summer*.—About three weeks at 18° C. to 25° C.

*Time to produce a rooted young plant, winter*.—About four weeks at 16° C. to 20° C.

*Root description*.—Fibrous.

*Rooting habit*.—Freely branching; medium density.

Plant description:

*Plant habit and form*.—Upright and mounded plant habit; inverted triangle; inflorescences positioned above the foliar plane; moderately vigorous growth habit.

*Plant height*.—About 42 cm.

*Plant diameter or spread*.—About 51 cm.

*Lateral branch description*.—Branching habit: Freely branching habit, about 13 lateral branches develop per plant. Length: About 31 cm. Diameter: About 5.5 mm. Internode length: About 5.8 mm. Aspect: Mostly upright to outwardly spreading. Strength: Strong. Texture: Smooth, glabrous. Color: Close to 143A; distally tinged with close to 63A.

*Leaf description*.—Arrangement: Alternate, simple. Length: About 10.8 cm. Width: About 6 cm. Shape: Ovate. Apex: Acute. Base: Truncate. Margin: Entire; slightly undulate. Venation pattern: Pinnate, reticulate. Texture, upper and lower surfaces: Pubescent. Color: Developing leaves, upper surface: Close to N137B. Developing leaves, lower surface: Close to 137C. Fully developed leaves, upper surface: Close to 139A; venation, close to 145C. Fully developed leaves, lower surface: Close to N138B; venation, close to 145C. Petioles: Length: About 3.2 cm. Diameter: About 1.9 mm. Texture, upper and lower surfaces: Pubescent. Color, upper and lower surfaces: Close to 77A.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—About twelve inflorescences develop per plant.

*Inflorescence diameter*.—About 17 cm.

*Inflorescence height*.—About 3 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering habit, plants flower about seven weeks under natural season conditions in Japan.

*Post-production longevity*.—Good post-production longevity; plants of the new *Euphorbia* maintain good substance and bract color for about six weeks.

*Flower bracts*.—Quantity per inflorescence: About 18. Length, largest bracts: About 5.8 cm. Width, largest bracts: About 3 cm. Shape: Ovate. Apex: Acute. Base: Truncate. Margin: Entire. Texture, upper surface: Smooth, glabrous. Texture, lower surface: Pubescent. Aspect: Mostly horizontal. Venation pattern: Pinnate, reticulate. Color: Transitional bracts, upper surface: Close to N137A and 63B. Transitional bracts, lower surface: Close to 138B. Developing bracts, upper surface: Close to N66A. Developing bracts, lower surface: Close to 68B. Fully expanded bracts, upper surface: Close to 50A; venation, close to 61A. Fully expanded bracts, lower surface: Close to 65A; venation, close to 149B. Flower bract petioles: Length: About 1 cm. Diameter: About 1.1 mm. Texture, upper and lower surfaces: Sparsely pubescent. Color, upper surface: Close to 149B.

*Cyathia*.—Quantity per corymb: About ten. Diameter of cyathia cluster: About 1.25 cm. Height, individual cyathium: About 6.5 mm. Diameter, individual cyathium: About 3.5 mm. Shape, individual cyathium: Globose; sessile. Color: Close to 59A. Nectaries: Quantity per cyathium: One. Size: About 1.3 mm by 2.5 mm. Color: Close to 182A.

*Peduncles*.—Length: About 2.5 mm. Diameter: About 1.8 mm. Strength: Strong. Aspect: Mostly upright to outward. Texture: Smooth, glabrous. Color: Close to 144A.

*Reproductive organs*.—Stamens: Quantity per cyathium: Numerous. Anther shape: Lanceolate or globose. Anther length: About 0.3 mm to 0.7 mm. Anther color: Close to 60C. Amount of pollen: None observed. Pistils: Plants of the new *Euphorbia* have not been observed to develop pistils. Seeds and fruits: Seed and fruit production has not been observed on plants of the new *Euphorbia*.

Disease & pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpri 9276' as illustrated and described.

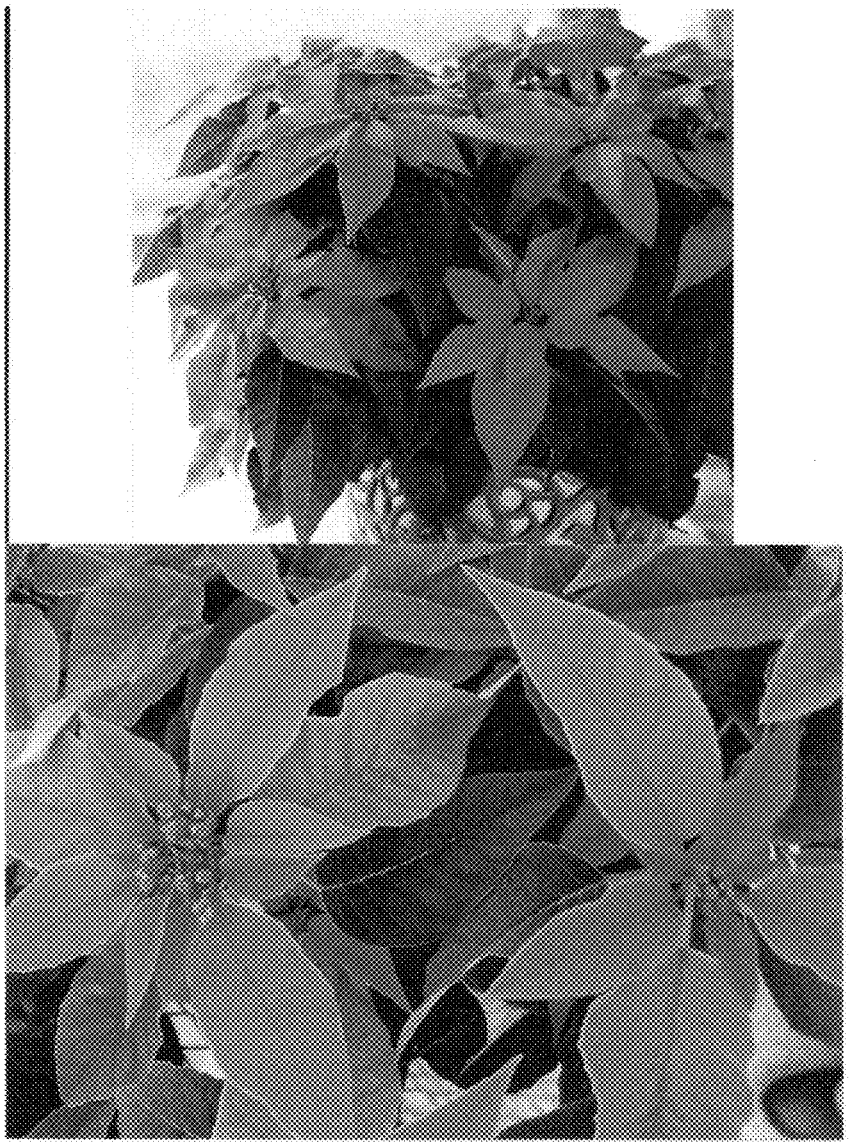

* * * * *